US 7,381,523 B2

(12) United States Patent
Efendic

(10) Patent No.: US 7,381,523 B2
(45) Date of Patent: Jun. 3, 2008

(54) METHODS FOR IDENTIFYING COMPOUNDS FOR TREATING DIABETES MELLITUS

(75) Inventor: Suad Efendic, Lidingo (SE)

(73) Assignee: BioCrine AB, Stockholm (SE)

( * ) Notice: Subject to any disclaimer, the term of this patent is extended or adjusted under 35 U.S.C. 154(b) by 0 days.

(21) Appl. No.: 11/510,232

(22) Filed: Aug. 25, 2006

(65) Prior Publication Data

US 2007/0003986 A1 Jan. 4, 2007

Related U.S. Application Data

(63) Continuation of application No. 11/123,895, filed on May 6, 2005, now abandoned.

(60) Provisional application No. 60/569,834, filed on May 10, 2004.

(51) Int. Cl.
*C12Q 1/00* (2006.01)
*G01N 33/567* (2006.01)
*A61K 38/29* (2006.01)

(52) U.S. Cl. .......................... 435/4; 435/7.21; 530/399

(58) Field of Classification Search ...................... None
See application file for complete search history.

(56) References Cited

U.S. PATENT DOCUMENTS

| 5,846,934 | A | 12/1998 | Bass et al. |
| 6,262,229 | B1 | 7/2001 | Coy et al. |
| 6,329,389 | B1 | 12/2001 | Suzuki et al. |
| 6,602,849 | B1 | 8/2003 | Gordon |
| 2001/0025097 | A1 | 9/2001 | Sheridan et al. |
| 2002/0052315 | A1 | 5/2002 | Hornik et al. |
| 2002/0128206 | A1 | 9/2002 | Hay et al. |

OTHER PUBLICATIONS

Abdel-Halim SM et al, Acta Physiol Scand, 148:219-226, 1993.
Alberti KG et al, Lancet 2:12199-1301, 1973.
Andersson A et al, Diabetologia 10:743-753, 1974.
Barden N et al, Endocrinology 101:635-638, 1977.
Bass RT et al, Mol Pharmacol. 50:709-715, 1996.
Baumbach et al., Mol Pharmacol 54:864-873, 1998.
Baum J et al, Diabetes 11:371-374, 1962.
Benali N et al, Digestion 62:27-32, 2000.
Boehm B et al, Best Pract Res Clin Gastroentrerol 16:493-509, 2002.
Boehm B, Expert Opin Investig Drugs 12:1501-1509, 2003.
Brunicardi FC et al, Pancreas 23:302-308, 2001.
Brunicardi FC et al, Pancreas 27:e84-e89, 2003.
Cejvan et al., Diabetes 52:1176-1181, 2003.
Cejvan K et al, Diabetes 51: S281-S384, 2002.
Crider AM, Mini Rev med Chem 2: 507-517, 2002.
Contour-Galera MO et al, Bioorg Med Chem Lett 11: 741-745, 2001.
Dasgupta, Elsevier, Pharmacology & Therapeutics, 102, 61-85, 2004.
Efendic S et al, FESB Lett 42:169-172, 1974.
Efedenic S et al, Acta Endocrinol 81:525-529, 1976.
Fagan et al, Surgery 124:254-259, 1998.
Goldsmith PC et al, Endocrinology 97: 1061-1064, 1975.
Goto Y et al, Tohoku J Exp Med, 119:85-90, 1976.
Goto Y et al, Proc Japan Acad 57:381-384, 1981.
Greenwood MT et al, Mol Pharmacol 52:807-814, 1997.
Hay B et al, Bioorg Med Chem Lett 11: 2731-2734.
Hannon J et al, J Mol Neurosci 18: 15-27, 2002.
Herbert V et al. J Clin Endocrinol Metab 25:1375-1384, 1965.
Hocart S et al, J Med Chem 42: 1863-1871, 1999.
Hokfelt T et al, Acta Endocrinol Suppl 200:5-41, 1975.
Hoog A et al, Endocrinology 137:2415-2423, 1996.
Howell SL et al, J Cell Biol 42: 695-705, 1969.
Hunyady B et al, Endocrinology 138:2632-2635, 1997.
Itoh M et al, Diabetes 29:693-696, 1980.
Janecka A et al, J Pept Res. 58: 91-107, 2001.
Kanatsuna T et al. Diabetes 30:231-234, 1981.
Kawai K et al, Science 218:477-478, 1982.
Kleinman R et al, Int J Pancreatol 18:51-57, 1995.
Koeslag JH et al, J Physiol 549:333-346, 2003.
Luft, Efendic et al. Med Biol 52:428-430, 1974.
Mattern RH et al, J Med Chem 41:2686-2692, 1998.
Mitra SW et al, Endocrinology 140:3790-3796, 1999.
Moinet C et al, Bioorg Med Chem Lett 11:991-995, 2001.
Norman M et al, Ann Surg 235: 767-774, 2002.
Nunn C et al, Eur J Pharmacol 465:211-218, 2003.
Orci L et al, Horm Metab Res 7: 400-402, 1975.
Ostenson CG et al, Diabetologia 36: 3-8, 1993.
Patel YC et al, Life Sci 57:1249-1265, 1995.
Patel YC, Front Neuroendocrinol 20:157-198, 1999.
Poitout L et al, J Med Chem 44:2990-3000, 2001.
Portela-Gomes GM et al, Appl Immunohistochem Mol Morphol, 8:126-132, 2000.
Portela-Gomes GM et al, Regul Pept 113:31-39, 2003.
Rajeswaran et al., J Med Chem 44:1305-1311, 2001.
Rajeswaran WG et al, Bioorg Med Chem 10:2023-2029, 2002.
Reichlin S et al, N Eng J Med 309: 1495-1501, 1983.
Reubi et al., Proc Natl Acad Sci USA 97:13973-978, 2000.
Rohrer et al, Science 282:737-740, 1998.

(Continued)

Primary Examiner—Ruixiang Li
(74) Attorney, Agent, or Firm—McDonnell Boehnen Hulbert & Berghoff LLP

(57) ABSTRACT

The invention is directed to methods for identifying candidate beta cell-sensitizing compounds comprising providing a pancreatic beta islet cell population derived from a diabetic subject, contacting the beta islet cell population with one or more somatostatin receptor 5-binding compounds, and identifying those somatostatin receptor 5-binding compounds that promote insulin secretion from the pancreatic beta islet cell population at a higher rate than from a control cell population. The invention is further directed to methods for treating type II diabetes comprising administering a beta cell-sensitizing compound identified by the first method of the invention to a diabetic patient in need of treatment.

2 Claims, 1 Drawing Sheet

OTHER PUBLICATIONS

Rossowski et al, Biochem Biophys Res Commun 197:366-371. 1993.
Rossowski et al., Biochem Biophys Res Commun 205:341-346, 1994.
Samols E et al, J Clin Invest 82:350-353, 1988.
Schuit FC at el, Diabetologia 32:207-212, 1989.
Schmitz O et al, Diabetes Metab 28:4S14-4S20, 2002.
Scicinski JJ et al, Bioorg Med Chem Lett, 8:3609-3614, 1998.
Sjojolm A et al, Pancreas 20:282-289, 2000.
Stark A Mentlein R, Regul Pept 108:97-102, 2002.
Stagner JI et al, Diabetes 37:1715-1721, 1988.
Stagner JI, Samols E, Diabetes 41: 93-97, 1992.
Stirnweis J et al, Peptides 23:1503-1506, 2002.
Strowski et al., Mol Endocrinol 17:93-106, 2003.
Taborsky GJ, Am Journ Physiol 245: E598-E603, 1983.
Tirone TA et al, Pancreas 26: e67-e73, 2003.
Wang, et al. Diabetes/Metabolism Research and Reviews, 21, 15-30, 2005.
Wilkinson et al., Br J Pharmacol 118:445-447, 1996.
Wilkinson et al., Eur J Pharmacol 340:277-285, 1997.
Wilkinson et al., Br J Pharmacol 121: 91-96, 1997.
Zambre et al., Biochem. Pharmacol. 57:1159-1164, 1999.

METHODS FOR IDENTIFYING COMPOUNDS FOR TREATING DIABETES MELLITUS

CROSS-REFERENCE TO RELATED APPLICATION

This application is a continuation of Ser. No. 11/123,895 filed May 6, 2005, now abandoned, and claims priority from the provisional application Ser. No. 60/569,834 filed May 10, 2004, incorporated by reference herein in its entirety.

BACKGROUND OF THE INVENTION

Diabetes mellitus is a complex chronic disorder that results primarily either from partial or complete lack of insulin secretion by the pancreas. The endocrine pancreas consists of the islets of Langerhans, which include several different cell types, including beta cells that are responsible for insulin secretion, alpha cells that produce glucagon, and delta cells that produce somatostatin (Luft, Efendic et al. Med Biol 52:428-430, 1974). Insulin and glucagon secreted from the beta and alpha cells serve to regulate blood glucose levels.

In diabetic patients, the pancreas produces insufficient or no insulin, the hormone which is responsible for the uptake of glucose into cells. As a result, the level of glucose in the blood becomes abnormally high. There are two main types of diabetes mellitus. In Type I diabetes mellitus, pancreatic beta cells are destroyed and insulin production ceases almost completely. Without regular injections of insulin the sufferer lapses into a coma and dies. Individuals suffering from Type I diabetes are totally insulin-dependent.

In patients with Type II diabetes, insufficient insulin is produced to maintain normal blood glucose levels. Often the body is resistant to the effects of insulin as the transduction of insulin signal is impaired. In most cases, insulin-replacement injections are not initially required. The combination of dietary measures, weight reduction and oral medication can keep the condition under control for a period of time, but most people with Type II diabetes ultimately require insulin injections.

While diabetes may be controlled with insulin and in some cases through careful diet or combinations of diet and oral medication, blood sugar levels fluctuate, sometimes dramatically, in diabetic patients irrespective of therapy. The pathological complications of diabetes are fundamentally related to hyperglycemia. If the diabetes is poorly controlled it can lead to diabetic complications. Such diabetic complications include nephropathy, neuropathy, retinopathy, heart disease, atherosclerosis, high blood pressure, stroke, and neurodegenerative conditions.

Intensive insulin treatment or treatments that produce insulin, such as sulfonylureas and glinides, increase the risk of hypoglycemia (or insulin shock), which occurs if blood glucose levels fall below normal. To date, FDA approved drugs that promote insulin secretion do so indiscriminately, at both high and low blood glucose levels, which can lead to hypoglycemia, discouraging the use of such drugs. Ongoing efforts in the pharmaceutical industry have identified genes and target molecules that participate in insulin expression and secretion. However, the identification of key molecular processes that regulate glucose-induced insulin expression and regulation requires knowledge of the complex inter-relationships of the metabolic pathways that govern this process.

Somatostatins are ubiquitous polypeptides known to affect basic biological processes such as growth, development, metabolism, and cell differentiation in vertebrates (US 20010025097). There are two major forms of somatostatin in mammals, SS-14, a 14 amino acid polypeptide (Ala-Gly-Cys-Lys-Asn-Phe-Phe-Trp-Lys-Thr-Phe-Thr-Ser-Cys) (SEQ ID NO:1), and SS-28 (Ser-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys) (SEQ ID NO:2), a 28 amino acid polypeptide. Both SS-14 and SS-28 are produced by proteolytic cleavage from larger precursors, and SS-14 is conserved among such mammals as monkeys, rats, cows, sheep, chickens and humans (US 20010025097).

The biological effects of somatostatin are apparently all inhibitory in nature, and are elicited upon receptor binding on a target cell. For example, somatostatin inhibits the pancreatic secretion of glucagon and insulin.

The effects of somatostatin on target cells are mediated by at least 5 classes of somatostatin receptors, SSTR1-SSTR5. SSTR2 and SSTR5 are the predominant subtypes in peripheral tissues. In rodents, somatostatin inhibits glucagon and insulin release via SSTR2 and SSTR5, respectively. Previous work has demonstrated that SS-14 interacts with SSTR1-5 with similar affinity, while SSTR5 displays a 10-fold higher affinity for SS-28 than SSTR1-4. SS-28 has been shown to preferentially inhibit insulin secretion from beta cells, and SS-14 inhibits the release of glucagon more potently than that of insulin.

Previous work has shown that an SSTR5 selective agonist inhibits glucose-stimulated insulin secretion from pancreatic islets isolated from normal rats and from normal mice (see, for example, (Rossowski et al., Biochem Biophys Res Commun 205:341-346, 1994). SSTR5 knockout mice indicate a role for SSTR5 in mediating pancreatic insulin secretion (Strowski et al., Mol Endocrinol 17:93-106, 2003). Antagonists for the somatostatin receptors, such as PRL-3195 (an SSTR5 antagonist) are known in the art. (Rajeswaran et al., J Med Chem 44:1305-1311, 2001).

Compounds that preferentially promote insulin release in response to hyperglycemia in Type II diabetes would represent a new class of drugs that minimize hypoglycemic episodes, and provide a pharmacological strategy with greater application and acceptance to improve glycemic control in Type II diabetic patients, and possibly decrease risk of developing diabetic complications, including but not limited to nephropathy, neuropathy, retinopathy, heart disease, atherosclerosis, high blood pressure, stroke, and neurodegenerative conditions, caused or exacerbated by poor glycemic control in diabetic patients.

SUMMARY OF THE INVENTION

The inventors of the present invention have unexpectedly found that SSTR5-selective antagonists selectively promote insulin secretion at elevated glucose levels in pancreatic islets isolated from Type II diabetic rats to a greater degree than they promote insulin release from these pancreatic islets isolated from normoglycemic animals. Thus, SSTR5-selective antagonists can act as "beta-cell sensitizers" and be used, for example, to promote glucose-induced insulin release in diabetic subjects while minimizing hypoglycemic episodes caused by indiscriminate promotion of insulin secretion regardless of glucose concentration.

In a first aspect, the present invention provides methods for identifying candidate pancreatic beta cell-sensitizing compounds comprising:

(a) providing a pancreatic beta-islet cell population derived from a diabetic subject, wherein the pancreatic beta islet cell population comprises pancreatic beta islet cells expressing somatostatin receptor 5;

(b) contacting the pancreatic beta-islet cell population with one or more somatostatin receptor 5-binding test compounds; and (c) identifying those somatostatin receptor 5 binding test compounds that promote insulin secretion from the pancreatic beta-islet cell population at a higher rate than from a control cell population, wherein such compounds are candidate pancreatic beta cell-sensitizing compounds.

In a preferred embodiment of this first aspect of the invention, the somatostatin receptor 5-binding test compounds are somatostatin receptor 5 antagonists.

In a further preferred embodiment of this first aspect of the invention, the contacting is carried out at an elevated glucose concentration.

In another preferred embodiment of this first aspect of the invention, the control cell population comprises pancreatic beta cells from a normoglycemic subject.

In another preferred embodiment, the method comprises identifying those candidate beta cell-sensitizing compounds that are also agonists of the somatostatin 2 receptor.

In a second aspect, the invention provides methods for treating type II diabetes comprising administering to a diabetic patient in need of treatment a beta cell-sensitizing compound identified by the methods of the first aspect of the invention.

DETAILED DESCRIPTION OF THE INVENTION

Figure 1:
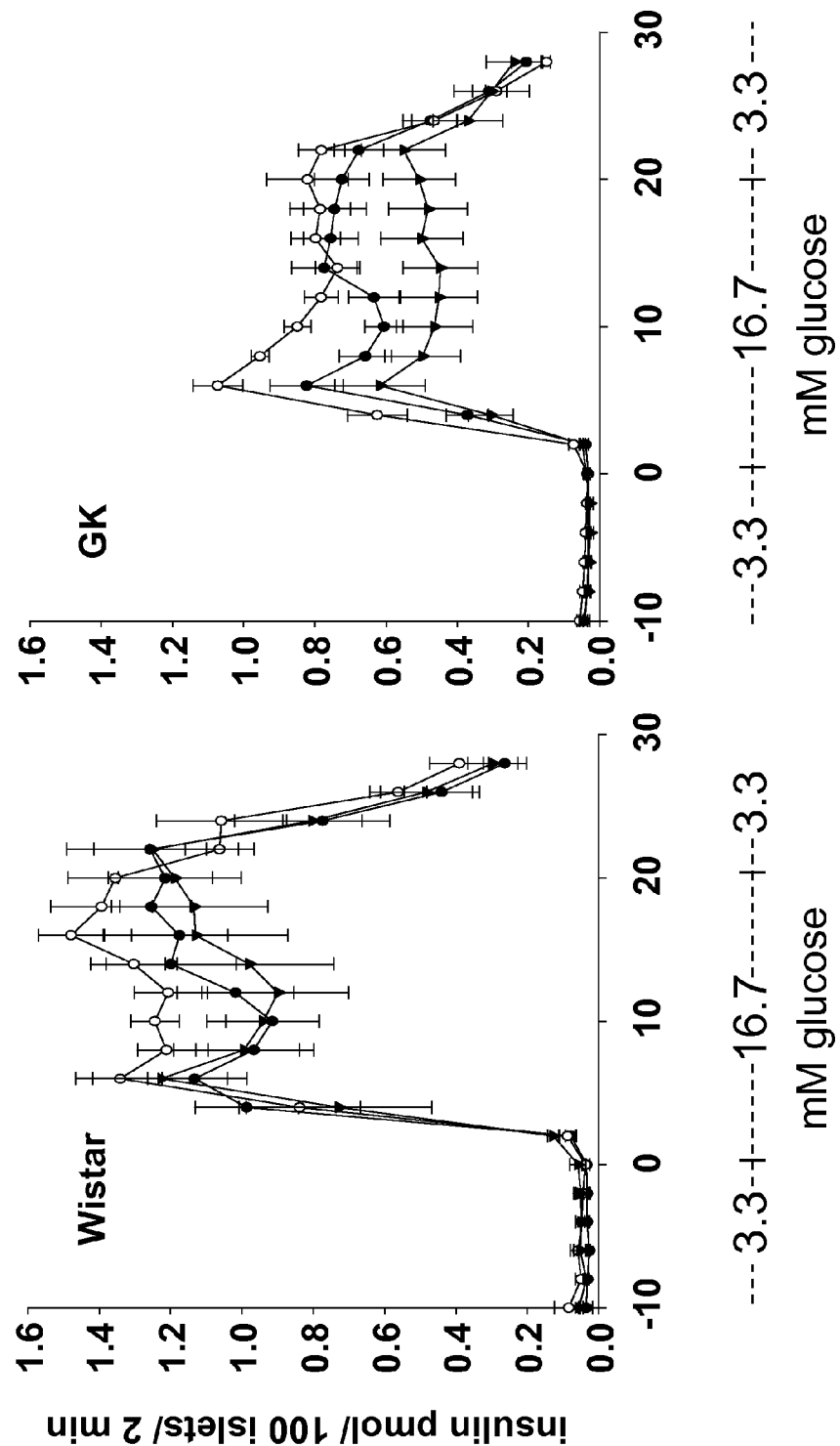
FIG. 1 provides an example of PRL-3195 stimulation of glucose-induced insulin release in perifused islets from diabetic (GK) and normoglycemic (Wistar) rats.

All references cited are herein incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney, 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise.

In one aspect, the present invention provides methods for identifying candidate pancreatic beta cell-sensitizing compounds comprising:

(a) providing a pancreatic beta-islet cell population derived from a diabetic subject, wherein the pancreatic beta islet cell population comprises pancreatic beta islet cells expressing somatostatin receptor 5;

(b) contacting the pancreatic beta-islet cell population with one or more somatostatin receptor 5-binding test compounds; and (c) identifying those somatostatin receptor 5 binding test compounds that promote insulin secretion from the pancreatic beta-islet cell population at a higher rate in Type 2 diabetes than from a control cell population, wherein such compounds are candidate pancreatic beta cell-sensitizing compounds.

As used herein, the term "pancreatic beta cell sensitizing compounds" means compounds that preferentially promote insulin release from pancreatic beta cells from diabetic subjects as compared to pancreatic beta cells from normoglycemic subjects. Any selective amount of increased insulin release in pancreatic beta cells from diabetic subjects, as opposed to indiscriminate insulin release, would be of great benefit in treating diabetic patients, while reducing the risk of hypoglycemia. In a preferred embodiment, insulin release is increased at least 5%, and preferably at least 10%, 15%, 20%, 25%, 30%, 40%, 45%, or 50% greater, or more, relative to control.

As used herein, the diabetic subject can be any mammal, preferably human.

As used herein, the diabetic subject suffers from type II diabetes, wherein the pancreatic beta cells still can produce insulin.

As used herein, the control cell population can be pancreatic beta cells from a non-diabetic subject contacted with test compounds, pancreatic beta cells from a diabetic subject contacted with control compounds, historical standards, or any other relevant control.

In a preferred embodiment, the contacting is performed at elevated glucose concentration, and the control comprises pancreatic beta cells from a normoglycemic subject.

As used herein the term "elevated glucose levels" means glucose concentrations of at least 6 mM, preferably between 6 mM and 50 mM, more preferably between 6 mM and 40 mM, more preferably between 7 mM and 30 mM, more preferably between 8 mM and 30 mM, and even more preferably between 8 mM and 25 mM. As used herein "normal glucose levels" means glucose concentrations of less than 6 mM, preferably between 3-5 mM.

As used herein the term "pancreatic beta islet cell population" means any population of cells (i.e.: two or more cells) that contains pancreatic beta islet cells. Such pancreatic beta islet cell populations include the pancreas, isolated pancreatic islets of Langerhans ("pancreatic islets"), and isolated pancreatic beta islet cells. Methods for the isolation of pancreas are well known in the art, and methods for isolating pancreatic islets, can be found, for example, in Cejvan et al., Diabetes 52:1176-1181, 2003; Zambre et al., Biochem. Pharmacol. 57:1159-1164, 1999; and Fagan et al., Surgery 124:254-259, 1998, and references cited therein. As known by those of skill in the art, pancreatic beta cells express SSTR5 (See, for example, Fagan et al., 1998). In a preferred embodiment, isolated pancreatic islets are used.

As used herein the term "contacting" means in vivo or in vitro, and (when in vitro) under suitable conditions for maintaining the pancreatic beta cell populations in organ cultures or tissue cultures, using appropriate media and/or perfusate conditions to promote binding of the SSTR5 antagonist to SSTR5. Such techniques are known to those of skill in the art. As used herein the "contacting" can occur at the time of initiating the culturing, or any time subsequent to initiating the culturing of the pancreatic beta cells. Such contacting can comprise adding the test compounds to a perfusate, adding the test compounds to cell/organ culture medium, or any other technique known in the art for contacting cells/organ cultures.

As used herein, compounds that "promote insulin secretion" are those that induce an increase in insulin secretion from the pancreatic beta cells compared to insulin secretion from the pancreatic beta cells seen in the absence of the test compounds. Any increase in insulin secretion over baseline levels is beneficial in diabetic patients in a hyperglycemic state, and thus the method does not require a specific amount of increase in insulin secretion from the pancreatic beta cells, so long as the compound(s) promotes insulin secretion from the pancreatic beta cells at a higher rate than control. As used herein "at a higher rate" means an increased amount of insulin secreted during the course of the experiment, preferably a statistically significant increase as indicated by standard statistical calculations.

Methods for conducting perifusion studies with pancreatic islets and perfusion studies with isolated pancreas, can be found, for example, in Cejvan et al., Diabetes 52:1176-1181, 2003, and references cited therein. For example, the pancreas from a diabetic rat may be isolated by standard methods and connected to an open non-recycling perfusion system to administer perfusion medium to the pancreas via a cannula inserted into the abdominal aorta, as described in Cejvan et al., 2003. Alternatively, pancreatic beta islets can be isolated from a pancreas from a diabetic rat by collagenase digestion, as described in Cejvan et al., 2003 and subject to perifusion as described in Cejvan et al., 2003. The resulting population of cells comprises pancreatic beta islet cells expressing somatostatin receptor 5. In either case, at least a first population of such cells and a second population of such cells is provided, one cultured at elevated glucose levels, and the other cultured at normal glucose levels, as defined above. Test compounds can be added to the cultures at the time of culturing, or subsequent to establishment of the cultures, as discussed above. The compounds can be added at various concentrations or for various time periods in order to assess different aspects of test compound activity, as is known by those of skill in the art. At desired time points, the insulin secretion from the first and second populations of cells is determined. Such methods for measuring insulin secretion are known in the art. See, for example, Fagan et al., 1998, and references cited therein.

The methods of the invention are used to identify SSTR5 antagonists that can act to selectively promote insulin secretion from pancreatic beta cells from diabetic subjects. However, the method of the invention does not require that only SSTR5 antagonists be used in the assay. For example, test compounds shown to bind to SSTR5 can be used in the assay, and those that are agonists are expected to inhibit insulin secretion, rather than promote insulin secretion, and thus will be selected against by the assay. Any method known in the art for identifying compounds that bind SSTR5 can be used, including but not limited to the use of membrane preparations from cells transfected to express SSTR5 at the cell surface. (See, for example, Baumbach et al., Mol Pharmacol 54:864-873, 1998; Rohrer et al, Science 282: 737-740, 1998; US 20020128206; U.S. Pat. No. 5,846,934). In a preferred embodiment, the binding of the test compounds against membrane preparations from cells expressing SSTR1-4 is also assessed, and those that show significantly higher binding affinities to SSTR5 than to any of SSTR1-4 are selected for. In a further preferred embodiment, the cells used are those that express little/no detectable SSTR5 prior to transfection, such as Chinese hamster ovary cells Alternatively, the test compounds used in the assay can include only those previously identified as antagonists of SSTR5. Any method known in the art for identifying a compound as an antagonist of SSTR5 can be used, including competitive binding assays in which various concentrations of test compounds are used to compete with SS-14 or SS-28 for binding to membrane preparations from SSTR5 expressing cells, such as recombinant cells expressing SSTR5. (See, for example, US 20020128206; US 20010025097; U.S. Pat. No. 5,846,934). In a preferred embodiment, the ability of test compounds to compete with SS-14 or SS-28 for binding to membrane preparations from cells expressing one of SSTR1-4 would also be assessed, and those that exhibit increased ability to compete SS-14 and/or SS-28 binding to SSTR5 than to any of SSTR1-4 would be selected for. In a further preferred embodiment, the cells used are those that express little/no detectable SSTR5 prior to transfection, such as Chinese hamster ovary cells. In a further preferred embodiment, SS-28 is used for competition experiments.

In further embodiments, SSTR5 antagonists are identified using methods including but not limited to the following (which can be used alone, or together with the methods disclosed above):

Identification of test compounds that bind to SSTR5 and that promote cAMP accumulation in test cells expressing SSTR5 compared to cAMP accumulation in the same cell types in the absence of the test compound(s). See, for example, Strowski et al., Mol Endocrinol 17:93-106, 2003; U.S. Pat. No. 5,846,934; Baumbach et al., 1998.

Identification of test compounds that bind to SSTR5 and that inhibit phospholipase C activity (Reubi et al., Proc Natl Acad Sci USA 97:13973-978, 2000) and/or inositol phosphate formation (Wilkinson et al., Br J Pharmacol 118:445-447, 1996) compared to phospholipase C activity and/or inositol phosphate formation in the same cell types in the absence of the test compound(s).

In a further embodiment, the SSTR5 antagonist compounds identified as beta cell sensitizers are also tested for SSTR2 agonist activity, and those with both types of activity are identified as a preferred class of beta cell sensitizers. Any method known in the art for identifying a compound as an agonist of SSTR2 can be used, including but not limited to the use of membrane preparations from cells transfected to express SSTR2 at the cell surface. (See, for example, Rohrer et al, Science 282:737-740, 1998; US 20020128206; US 20010025097; U.S. Pat. No. 5,846,934).

In a further embodiment, the method comprises synthesizing the compounds identified in the assay, using standard methods in the art.

In a further aspect, the present invention provides methods for treating type II diabetes, comprising administering to a diabetic patient a beta cell sensitizer identified by the assay disclosed above, in any embodiment thereof, to promote improved glycemic control in the diabetic patient. In one embodiment, the method comprising administering an SSTR5 antagonist to the patient. In a further embodiment, the method comprises administering an SSTR5 antagonist and an SSTR2 agonist to the patient. In this embodiment, the SSTR5 antagonist and the SSTR2 agonist can be separate compounds, or they can be the same compound, identified as disclosed above.

EXAMPLES

Animals

Male Wistar rats, aged 2-3 months, were obtained from B&K Universal (Sollentuna, Sweden). The animals were fed ad libitum with free access to water and placed in rooms with alternate 12 hour periods of light and darkness. GK rats came from Stockholm's colony which was established 1992

Isolation of Pancreatic Islets, Batch Incubation, and Perifusion Studies.

Islets were isolated by digestion with collagenase (Hoffmann-La Roche, Basel, Switzerland) and cultured for 20-22 h in RPMI-1640 medium supplemented with 11 mmol/l glucose and 10% (vol/vol) FCS. For both batch and perifusion studies, the islets were first preincubated for 35 min in Krebs-Ringer bicarbonate buffer (KRBB) containing 3.3 mmol/l glucose and 2 g/l bovine plasma albumin (Sigma, St. Louis, Mo.).

For batch incubations, batches of ten islets were then incubated for 1 h in 350 µl KRBB-albumin-glucose. As a stimulus for hormone release, 3.3 to 25 mM glucose or 20 mM arginine were used. PRL-3195 (Rajeswaran et al., J. Med. Chem. 44:1305-1311, 2001) was added to incubations with glucose and arginine at a concentration of 10 µM. After each incubation, 100 µl aliquots of incubation medium were stored at −20° C. for subsequent radioimmunoassay of insulin (Herbert V et al. J Clin Endocrinol Metab 25:1375-1384, 1965).

For perifusion, following culture and preincubation, 100 islets were added to each of two perifusion chambers by layering between inert polystyrene beads (Bio-Gel 200-400 mesh; Bio-Rad Laboratories, Richmond, Calif.). This perifusion system has been previously described (Kanatsuna T et al. Diabetes 30:231-234, 1981)., The KRBB-albumin-glucose with the flow rate of 0.4 ml/2 min was used as a basal perifusion medium. The perifusion protocol was started by a 30-min equilibration period with basal medium, followed by a 20-min stimulation period, and finally by a 10-min reperifusion with the basal medium. Glucose at a concentration 16.7 mM was used as the stimulus for insulin release. Simultaneously with 16.7 mM glucose was administered somatostatin receptor 5 antagonist (PRL-3195) at 10 or 50 µM. Samples were collected at 2-min intervals, ice-chilled immediately, frozen, and kept at −20° C. for subsequent radioimmunoassay of insulin (Herbert V et al. J Clin Endocrinol Metab 25:1375-1384, 1965).

Insulin Release From Isolated Islets in Batch Incubations.

When batch-incubated islets from normoglycemic (Wistar) rats were incubated at increasing glucose concentrations, there was a clear stimulation of insulin release (Table 1). In rats with Type II diabetes (GK), insulin release was not significantly different from the normoglycemic (Wistar) rats at 3.3 mM glucose. With increasing glucose concentrations, however, insulin release from GK rat islets increased, but to an extent that was markedly less than that of Wistar rats. The addition of the SSTR5 antagonist PRL-3195 at a concentration of 10 µM to islets from Wistar and GK rats increased insulin release at all glucose concentrations. This effect of PRL-3195 was, however, more pronounced in GK rats.

At 3.3 mM glucose, 20 mM arginine significantly stimulated insulin release from Wistar and GK rat islets. This response was, however, significantly less for GK rat islets (P<0.001). The addition of PRL-3195 significantly stimulated insulin release in both cases.

Insulin Release From Isolated Perifused Islets.

To examine insulin release under more physiological conditions, the effect of the SSTR5 antagonist PRL-3195 was tested in perifused islets. In perifused islets from normoglycemic rats (Wistar), there was a marked and biphasic insulin response when the glucose concentration was increased from 3.3 to 16.7 mM. This response was, however, at 9.14 pmol/100 islets, significantly less (p=0.02) in GK rat islets than in Wistar islets which released 19.8 pmol/100 islets during the stimulation period (FIG. 1). When 10 µM PRL-3195 was added to the perifusion medium, the insulin response to glucose was not significantly increased in islets from either Wistar or GK rats. However, 50 µM PRL-3195 significantly enhanced the insulin release evoked by 16.7 mM glucose in perifused GK islets to 15.3 pmol/100 islets (p=0.049), whereas in islets from Wistar rats there was no significant effect.

The results from the batch incubation and perifusion studies indicate that an SSTR5 antagonist is more effective at promoting glucose-induced insulin secretion from islet cells derived from Type II diabetic rats as compared to islets from Wistar rats. Importantly the antagonist is less effective at promoting insulin secretion from islet cells derived from both normoglycemic rats and Type II diabetic rats when the islet cells are exposed to normal glucose concentrations. Thus, SSTR5-selective antagonists are promising compounds for the treatment of diabetes. These SSTR5-selective antagonists are able to promote glucose-induced insulin release in diabetic subjects while minimizing hypoglycemic episodes caused by indiscriminate promotion of insulin secretion regardless of glucose concentration.

The complete disclosures of all patents, patent applications including provisional patent applications, and publications cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

TABLE 1

The effect of 10 µM PRL 3195 on insulin release at various concentrations of glucose in batch incubated islets from Wistar and GK rats.

| Glucose mM | Wistar | | | GK | | |
|---|---|---|---|---|---|---|
| | control | +PRL-3195 | % increase | control | +PRL-3195 | % increase |
| 3.3 | 0.186 ± 0.03 | 0.337.5 ± .02* | 79.2 | 0.166 ± 0.02 | 0.287 ± 0.03** | 72.6 |
| 8.3 | 0.372 ± 0.03 | 0.917 ± .14** | 142 | 0.244 ± 0.02 | 0.824 ± 0.05** | 228 |
| 16.7 | 2.22 ± 0.17 | 3.83 ± 0.21** | 72.7 | 0.638 ± 0.06 | 1.90 ± 0.16** | 197 |
| 25 | 3.17 ± 0.21 | 4.26 ± 0.17** | 34.4 | 0.663 ± 0.05 | 2.59 ± 0.21** | 291 |

Data were obtained from batch incubations with or without the addition of 10 µM PRL 3195, and are presented as pmol insulin/islet-hour$^{-1}$ at the means ± SE of 5-6 experiments with 3 observations in each experiment.
*P = 0.008;
**P < 0.001.

I claim:

1. A method for identifying candidate pancreatic beta cell-sensitizing compounds comprising:
   (a) providing a pancreatic beta-islet cell population derived from a diabetic subject, wherein the pancreatic beta islet cell population comprises pancreatic beta islet cells expressing somatostatin receptor 5;
   (b) contacting the pancreatic beta-islet cell population with one or more somatostatin receptor 5-binding test compounds, wherein the contacting is performed at a glucose concentration of between 8 mM and 30 mM; and
   (c) identifying those somatostatin receptor 5-binding test compounds that promote insulin secretion from the pancreatic beta-islet cell population to a greater degree than from a control pancreatic beta-islet cell population from a normoglycemic subject, wherein such compounds are candidate pancreatic beta cell-sensitizing compounds.

2. The method of claim 1, wherein the somatostatin receptor 5-binding test compounds are somatostatin receptor 5 antagonists.

* * * * *

```
                         SEQUENCE LISTING

<160> NUMBER OF SEQ ID NOS: 2

<210> SEQ ID NO 1
<211> LENGTH: 14
<212> TYPE: PRT
<213> ORGANISM: artificial sequence
<220> FEATURE:
<223> OTHER INFORMATION: synthetic peptide

<400> SEQUENCE: 1

Ala Gly Cys Lys Asn Phe Phe Trp Lys Thr Phe Thr Ser Cys
1               5                   10

<210> SEQ ID NO 2
<211> LENGTH: 28
<212> TYPE: PRT
<213> ORGANISM: artificial sequence
<220> FEATURE:
<223> OTHER INFORMATION: synthetic peptide

<400> SEQUENCE: 2

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25
```